United States Patent
Enomoto et al.

(10) Patent No.: US 7,829,740 B2
(45) Date of Patent: Nov. 9, 2010

(54) PROCESS FOR PRODUCTION OF LACTIC ACID AND EQUIPMENT FOR THE PRODUCTION

(75) Inventors: Heiji Enomoto, 5-16, Kagitori 4-chome, Taihaku-ku, Sendai, Miyagi (JP) 982-0804; Fangming Jin, Shanghai (CN); Takehiko Moriya, Sendai (JP); Kenji Kakeda, Izumiotsu (JP); Yoshitoshi Sekiguchi, Maizuru (JP); Hisanori Kishida, Osaka (JP)

(73) Assignees: Heiji Enomoto, Sendai-shi (JP); Hitachi Zosen Corporation, Osaka-shi (JP); Tohoku Electric Power Co., Inc., Sendai-shi (JP)

( * ) Notice: Subject to any disclaimer, the term of this patent is extended or adjusted under 35 U.S.C. 154(b) by 0 days.

(21) Appl. No.: 11/994,263

(22) PCT Filed: Jun. 29, 2006

(86) PCT No.: PCT/JP2006/312967

§ 371 (c)(1),
(2), (4) Date: May 28, 2008

(87) PCT Pub. No.: WO2007/001043

PCT Pub. Date: Jan. 4, 2007

(65) Prior Publication Data

US 2009/0088589 A1 Apr. 2, 2009

(30) Foreign Application Priority Data

Jun. 29, 2005 (JP) .............................. 2005-189182

(51) Int. Cl.
*C07C 59/08* (2006.01)

(52) U.S. Cl. ...................................................... 562/589
(58) Field of Classification Search ........................ None
See application file for complete search history.

(56) References Cited

U.S. PATENT DOCUMENTS 5,034,105 A * 7/1991 Berglund et al. ............ 204/538

FOREIGN PATENT DOCUMENTS

| EP | 0 523 014 A2 | 1/1993 |
|---|---|---|
| JP | 4-356436 | 12/1992 |
| JP | 11-342379 | 12/1999 |
| JP | 2005-200340 | 7/2005 |

OTHER PUBLICATIONS

Hisanori Kishida, et al. "Conversion of Glycerin into Lactic Acid by Alkaline Hydrothermal Reaction" Chemistry Letters, vol. 34, No. 11, 2005, pp. 1560-1561.

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

A process for producing lactic acid according to the invention is characterized in that glycerin is subjected to a hydrothermal reaction under an alkaline condition at a temperature in the range of 150 to 400° C. and under pressure equal to or more than the saturated vapor pressure at the temperature. The glycerin produced from plant fats, animal fats or the like or pure product synthesized chemically or a discharge containing glycerin generated at the production of diesel fuel oil from fats, in which the fats are subjected to a transesterification with alcohol in the presence of an alkali catalyst in order to obtain fatty acid ester is preferably used as a starting material.

14 Claims, 7 Drawing Sheets

PROCESS FOR PRODUCTION OF LACTIC ACID AND EQUIPMENT FOR THE PRODUCTION

TECHNICAL FIELD

The invention relates to a process for producing lactic acid from glycerin as a raw material and an apparatus for producing lactic acid.

BACKGROUND ART

Recently, in Europe, U.S.A and other countries, a diesel fuel oil produced from a plant oil as a raw material (so-called a bio-diesel fuel: BDF) is actively produced. Such a diesel fuel oil is composed of a fatty acid ester taken out from a fat consisting of a triester of glycerin by performing a transesterification of the fat with alcohol in the presence of an alkaline catalyst. In this technology, the fatty acid ester taken out from fats can be effectively used as a bio-diesel fuel oil. However, glycerin containing the alkaline catalyst is generated as a by-product at the production thereof in an amount of substantially 1/10 of the raw material by weight; accordingly, there is a problem in how to process the glycerin containing the alkaline catalyst.

Lactic acid is a raw material of plastics (lactic acid polymer). The lactic acid polymer is considered as a material which is applicable to sheets used for agriculture or civil engineering, packages, shopping bags, car interiors and so on. Since the lactic acid polymer is a biodegradable material (a material which can be decomposed by microorganisms), it is gathering attention as one of solutions of a waste disposal. Furthermore, since the lactic acid polymer is derived from organisms, it is gathering an attention in the saving of the petroleum resources and in the reduction of a generation amount of $CO_2$.

Accordingly, in the current situation where the wastes are increasing, from the viewpoint of reducing an amount of wastes as well, the lactic acid polymer is gathering attention and expected to increase in future demand.

As a conventional process for producing lactic acid that is a raw material of lactic acid polymer-based plastics, a fermentation process and a synthesis process can be cited.

The fermentation process is a process where sucrose, glucose, starch or the like derived from cultivated plants such as corns, sugarcanes, cassayas and so on are used as raw materials and converted into lactic acid by a fermentation action of lactic bacteria.

As the synthesis process, the following processes can be cited: (i) a process where hydrocyanic acid is allowed to react with acetaldehyde to produce cyanohydrin, followed by hydrolyzing the resultant product to obtain lactic acid, and (ii) a process where acetaldehyde is allowed to react with carbon monoxide under high pressure to obtain lactic acid.

However, in both processes, there is a problem in that the cost price of lactic acid becomes high since expenses for obtaining lactic acid (such as land and cultivation period for cultivating cassayas and so on, a time period necessary for fermenting sugars, a large-scale fermentation tank necessary for fermentation, disposal of waste generated after lactic acid was obtained and so on) are very large; accordingly a process for inexpensively obtaining lactic acid is in demand.

Glycerin is produced as a by-product when the bio-diesel fuel oil is produced as mentioned above. Furthermore, it is a constituent element of fats such as plant fats, animal fats and so on and contained a lot in a natural world. That is, in an industrial field relating to fats, glycerin can be produced by a removal from various kinds of fats and can be procured in a large amount.

Accordingly, if lactic acid can be produced by a process using glycerin which is a material capable of being inexpensively procured, such a process is desirable because the cost for producing lactic acid can be reduced.

A patent document JP-A-11-342379 discloses a process for obtaining organic acids from a fish meat. The process for producing organic acids according to the Document uses a fish meat as a raw material and lactic acid is cited as one of organic acids obtained variously.

However, according to the process, the resultant lactic acid is a by-product and is produced as one of organic acids obtained variously. That is, the process is not an efficient process for obtaining lactic acid.

Patent Document 1: JP-A-11-342379

DISCLOSURE OF THE INVENTION

Problem to be Solved by the Invention

The present invention was made in view of the above-mentioned situations and intends to provide a process for inexpensively producing lactic acid of which demand is industrially expected, in which glycerin obtained from a wide range including pure products, food waste oil and the like is used.

Means for Solving the Problem

In order to overcome the above mentioned problem, a process for producing lactic acid according to the present invention is characterized in that glycerin is subjected to a hydrothermal reaction under an alkaline condition.

In the process according to the invention, the glycerin produced from plant fats, animal fats or the like or pure product synthesized chemically is preferably used as a starting material.

In the process according to the invention, as the glycerin, a discharge containing glycerin generated at the production of a diesel fuel oil from fats, in which the fats are subjected to a transesterification with alcohol in the presence of an alkaline catalyst in order to obtain fatty acid ester, is preferably used as a raw material.

In the process according to the invention, the process comprises a step of performing a gas-liquid separation where an alkali solution containing lactic acid is separated from a hydrogen gas, both of which are generated in the hydrothermal reaction.

In the process according to the invention, preferably, the process further comprises a step of concentrating lactic acid and an alkaline component present in an aqueous solution after the hydrothermal reaction according to an electrodialysis process.

In the process according to the invention, preferably, the process further comprises a step of separating lactic acid from the alkaline component present in the aqueous solution after the hydrothermal reaction according to an electrodialysis process with a bipolar membrane.

In the process according to the invention, an alkaline component for making the glycerin under an alkaline condition is preferably supplied when the hydrothermal reaction is carried out.

In the process according to the invention, the alkaline component is preferably supplied in several times.

In the process according to the invention, the alkaline component separated from the alkaline solution containing lactic acid is preferable used.

In the process according to the invention, unreacted glycerin dissolved in a solution containing the alkaline component is preferably recovered in order to reuse it as a raw material for lactic acid.

In the process according to the invention, a generated hydrogen gas is preferably used as a gas to be used for a fuel battery.

Furthermore, an apparatus for producing lactic acid according to the invention is equipped with a reactor where glycerin is subjected to a hydrothermal reaction under an alkaline condition, wherein a set of procedures from a supply of an alkaline solution containing glycerin to a production of lactic acid are continuously carried out.

In the apparatus according to the invention, preferably, the apparatus is further equipped with a gas-liquid separator that separates an alkaline solution containing lactic acid from a hydrogen gas, generated in the reactor.

In the apparatus according to the invention, preferably, the apparatus is further equipped with an electrodialysis unit with a bipolar membrane that separates an alkaline solution containing lactic acid from the gas-liquid separator into a solution containing lactic acid and an alkaline solution.

In the apparatus according to the invention, preferably, the apparatus is further equipped with a calcium crystallizer that separates an alkaline solution containing lactic from the gas-liquid separator into a solid of calcium lactate and an alkaline solution according to a crystallization process.

EFFECT OF THE INVENTION

According to the invention, following effects can be obtained.

(1) Lactic acid can be produced from glycerin discarded from plants for a bio-diesel, oleochemical plants and so on as a raw material. (so far, crops have to be cultivated).

(2) In many cases, an alkali used as a catalyst is contained in the glycerin discarded from plants for bio-diesel, oleochemical plants and so on, but such alkali can also be used efficiently in the present invention.

(3) A time required for a conversion of glycerin into lactic acid is from several minutes to several hours (an existing fermentation process necessarily takes a reaction time of several days).

(4) A conversion rate of lactic acid from glycerin is such high as 90% and a reaction by-product is scarce. Accordingly, treatment of waste water is relatively easily applied (in an existing fermentation process, a culture solution for lactic acid fermenter has to be treated).

BEST MODE FOR CARRYING OUT THE INVENTION

In what follows, methods for utilizing a discharge containing glycerin will be described in detail with reference to the drawings.

Embodiment 1

FIG. 1 is a flow sheet explaining a process performed using a continuous reactor that is an example of a process for producing lactic acid in accordance with the present invention.

In the process for producing lactic acid according to the present invention, in the beginning, glycerin that is a raw material is introduced into a tank for storing a raw material (1) together with water and an alkaline component such as sodium hydroxide or the like. An alkaline solution containing glycerin stored in the tank for storing a raw material (1) goes through a high-pressure pump (2), a pre-heater (3), a reactor (4) and a cooler (5) sequentially, and, after going through a valve for controlling a pressure (7), finally reaches a tank for storing an alkaline solution containing lactic acid (6).

The respective configurations are described bellow.

The tank for storing a raw material (1) is a tank where an alkaline solution containing a desired amount of glycerin and having desired alkalinity is prepared by adding appropriate amount of glycerin, an alkaline component and water, respectively.

Glycerin added to the tank for storing a raw material (1) may be a product derived from a decomposition of fats such as plant fats, animal fats or the like or a pure product synthesized chemically. Alternatively, glycerin as a raw material may contain impurities. For instance, as such a glycerin containing impurity, glycerin contained in fats that can be recovered from rendering of fish meats and animal meats, or discharge from plants for a bio-diesel fuel oil, plants for soap and so on can be cited.

A concentration of glycerin is in the range of 1 to 80% by weight and preferably 50% by weight or less from the viewpoint of improving the fluidity owing to lowering of the viscosity.

As the alkaline component, any alkaline substances can be used. Examples thereof include sodium hydroxide, potassium hydroxide, ammonia and so on. Furthermore, a basic solid catalyst such as calcium hydroxide can be used as well. A preferable concentration of an alkaline component is in the range of 0.1 to 50%.

The high-pressure pump (2) applies predetermined pressure on the alkaline solution containing glycerin from the tank for storing a raw material (1) and water is supplied quantitatively.

The pre-heater (3) preliminarily heats the alkaline solution containing glycerin before it is introduced in a reactor (4) where a reaction is carried out under a high temperature and high pressure condition. The pre-heater (3) may have a heater for preliminarily heating. Alternatively, the alkaline solution containing glycerin may be heated by a heat exchange at a cooler (5) provided downstream of the reactor (4).

In the reactor (4), the alkaline solution containing glycerin is put under a high temperature and high pressure condition to convert glycerin in the alkaline solution to lactic acid. Specifically, a temperature is set in the range of 150 to 400° C. and pressure is set at pressure equal to or more than the saturated vapor pressure of water at the above temperature range so that water may retain in a liquid phase.

When a reaction is carried out at certain temperature at pressure lower than saturated vapor pressure of water, all water vaporizes and thereby an alkaline component precipitates as a solid salt. In the reaction, glycerin is reacted with a hydroxide ion OH⁻ in an aqueous solution having alkalinity to convert it into lactic acid; accordingly, unless in a state where water retains a liquid phase, a reaction is difficult to proceed. Accordingly, a reaction pressure is desirably set to a pressure equal to or more than the saturated vapor pressure at a reaction temperature. A reaction time is largely different depending on a reaction temperature. The higher the reaction temperature is, or the higher the alkaline concentration is, the shorter the reaction time for converting it into lactic acid is.

Glycerin in the alkaline solution is converted into lactic acid by a reaction in the reactor (4). After cooled by the cooler (5), the resultant alkaline solution containing lactic acid is transported to the tank for storing an alkaline solution containing lactic acid (6) and stored in the tank for storing an alkaline solution containing lactic acid (6). The valve for controlling a pressure (7) is disposed between the reactor (4) and the tank for storing an alkaline solution containing lactic acid (6) and the high-pressure state of the alkaline solution is released by the valve (7).

The alkaline solution containing lactic acid stored in the tank for storing an alkaline solution containing lactic acid (6) can be efficiently concentrated using an electrodialysis unit when concentrations of lactic acid and alkaline component are low. Furthermore, in the case where lactic acid and alkaline component have to be separated, the alkaline solution containing lactic acid stored in the tank for storing an alkaline solution containing lactic acid (6) can be separated into lactic acid and alkaline component according to a separator with a bipolar membrane. Still furthermore, in the case where lactic acid and a salt of alkaline component want to be taken out as solids from the alkaline solution containing lactic acid stored in the tank for storing an alkaline solution containing lactic acid (6), lactic acid and the salt of alkaline component can be taken out as solids according to a crystallizer.

Embodiment 2

FIG. 2 is a flow sheet explaining the apparatus for producing lactic acid according to embodiment 2.

In the apparatus for producing lactic acid according to embodiment 2, in the beginning, a discharge containing glycerin from BDF plants, oleochemical plants and so on is introduced as a raw material to a tank for storing a raw material (1). The discharge containing glycerin from BDF plants or the like as a raw material contains an alkaline component. When a content of the alkaline component is scarce, an alkaline component such as NaOH or the like is added appropriately. Furthermore, when an amount of water is scarce, water is appropriately added.

An alkaline solution containing glycerin stored in the tank for storing a raw material (1), after water is appropriately added thereto, goes through a high-pressure pump (2), a heat exchanger (3), a reactor (4), the heat exchanger (3), a valve for controlling a pressure (7) sequentially and is finally supplied to a gas-liquid separator (5) to separate here the solution into an alkaline solution containing lactic acid and a hydrogen gas. The tank for storing a raw material (1), the high-pressure pump (2) and the reactor (4), shown in FIG. 2, are the same as those of embodiment 1 shown in FIG. 1; accordingly detailed explanations thereof are omitted.

In the apparatus for producing lactic acid according to embodiment 2, after pressurized to predetermined pressure by the high-pressure pump (2), the alkaline solution containing glycerin stored in the tank for storing a raw material is supplied to the heat exchanger (3) to undergo heat-exchange with a gas-liquid mixture fluid (described later) after the hydrothermal reaction. Thereafter, the alkaline solution containing glycerin heated in the heat exchanger (3) is supplied to the reactor (4).

Glycerin supplied to the reactor is heated by a heating medium (overheated water vapor, silicone oil or the like) transported from a heater for the heating medium (6) in order to be maintained at a predetermined temperature and to undergo a hydrothermal reaction, which leads to a decomposition of glycerin into lactic acid and a hydrogen gas.

The fluid composed of a gas-liquid mixture leaves the reactor (4). The fluid is heat-exchanged with the alkaline solution containing glycerin to be supplied to the reactor (4) in order to lower a temperature and is depressurized by the valve for controlling a pressure (7) and then supplied to the gas-liquid separator (5). Since a gas component generated by the hydrothermal reaction in the reactor (4) is almost hydrogen, a pure hydrogen gas can be obtained at the gas-liquid separator (5). In addition, since a liquid component generated by the decomposition of glycerin is almost alkaline solution containing lactic acid, a pure alkaline solution containing lactic acid can be obtained. The hydrogen gas and the alkaline solution containing lactic acid obtained by the above reaction are taken out from the apparatus after adjusting their pressures using valves for controlling a pressure (8) and (9), respectively.

Embodiment 3

FIG. 3 is a flow sheet explaining the apparatus for producing lactic acid according to embodiment 3.

The apparatus for producing lactic acid according to the embodiment has the same constituents as those of the apparatus for producing lactic acid according to the above mentioned embodiment 2; accordingly, in the description below, the same constituents as those of the apparatus for producing lactic acid according to embodiment 2 are provided with the same reference numerals and detailed explanations are omitted.

In the apparatus for producing lactic acid according to embodiment 3, a discharge containing glycerin from BDF plants, oleochemical plants and so on is introduced as a raw material into the tank for storing a raw material (1)

An alkaline solution containing glycerin stored in the tank for storing a raw material (1), after water is appropriately added thereto, goes through a high-pressure pump (2), the heat exchanger (3), the reactor (4) and the heat exchanger (3) sequentially. After going through a valve for controlling a pressure (7), the solution is finally supplied to a gas-liquid separator (5) to separate the solution into a solution containing sodium lactate and a hydrogen gas. The solution containing sodium lactate obtained by separation in the gas-liquid separator (5) is supplied to an electrodialysis unit with a bipolar membrane (10) in order to separate the solution into a solution containing lactic acid and an NaOH solution. The resultant NaOH solution is supplied to the reactor (4) after storing in the tank for storage (11).

The apparatus for producing lactic acid according to embodiment 3 is different from the apparatus for producing lactic acid according to embodiment 2 in that NaOH is supplied to the reactor (4) instead of the tank for storing a raw material (1). This is because the heat exchanger (3) and the high-pressure pump (2) may be inhibited from corrosion due to high concentration of NaOH. As a reaction proceeds, lactic acid is generated and consumed by neutralization with NaOH; accordingly, NaOH is supplied to the reactor (4) in several times. Such supply of NaOH in several times prevents the reactor (4) from corrosion due to high concentration of alkali as well.

The aqueous solution containing sodium lactate from the gas-liquid separator (5) has potentially a use as a raw material for moisturizing agents and chemicals. In the case where it is used as a raw material for polylactic acid, a separation of the solution into lactic acid and sodium component has to be performed. In the apparatus for producing lactic acid according to embodiment 3, the aqueous solution containing sodium lactate obtained by a separation at the gas-liquid separator (5) is separated into a solution containing lactic acid and an NaOH solution in the dialysis unit with a bipolar membrane (10). The NaOH solution obtained by the separation using the dialysis unit with a bipolar membrane (10) is supplied to the reactor (4) after stored in a tank for storage (11). Alternatively, the NaOH solution obtained by the separation may be reused as a catalyst for a transesterification of fats.

Embodiment 4

FIG. 4 is a flow sheet explaining the apparatus for producing lactic acid according to embodiment 4.

The apparatus for producing lactic acid according to the embodiment has the same constituents as those of the apparatus for producing lactic acid according to embodiment 2; accordingly, the same constituents as those of the apparatus for producing lactic acid according to embodiment 2 are provided with the same reference numerals and the detailed explanations are omitted.

In the apparatus for producing lactic acid according to embodiment 4, after the gas-liquid separation of the solution into a solution containing sodium lactate and a hydrogen gas in the gas-liquid separator (5), the solution containing sodium lactate obtained by the separation is supplied to a calcium crystallizer (12).

The addition of calcium hydroxide in the calcium crystallizer (12) results in a precipitation of salt of calcium lactate according to a formula bellow. The precipitated salt is separated from an NaOH solution according to a solid-liquid separation.

$$2CH_3CH(OH)COONa + Ca(OH)_2 \rightarrow (CH_3CH(OH)COO)_2Ca\downarrow + 2NaOH$$

The NaOH solution obtained by the separation is supplied to the tank for storing a raw material (1) after stored once in a storage tank (13). The NaOH solution obtained by the separation at the calcium crystallizer (12) dissolves unreacted glycerin. A supply of the NaOH solution to the tank for storing a raw material (1) leads to a recycle of the unreacted glycerin; accordingly, the efficiency for a production of lactic acid can be improved.

The hydrogen gas generated using the apparatus for producing lactic acid shown in each of embodiments may be combusted as an off-gas by a flare stack or the like. Alternatively, since the hydrogen gas generated by each of the processes has high purity as mentioned above, it may be recovered in order to use as a gas for fuel batteries, hydrogen engines and so on.

The lactic acid generated using the apparatus for producing lactic acid shown in each of the embodiments has a racemic form in which optical isomers of L and D forms are equally mixed. In order to make use of lactic acid as a raw material of polylactic acid, an optical resolution process (racemic resolution) has to be applied to separate the mixture into an L form and a D form. In the optical resolution process, known resolution processes such as a chromatography process, a preferential crystallization process, a diastereoisomer process, an inclusion complex process and the like can be made use of.

In the following examples, the present invention is explained specifically.

Example 1

In example 1, a tube made of SUS316 as shown in FIG. 5 and sealed air-tightly with caps was used as a reactor (10). A volume thereof is 10 ml, an allowable temperature limit is 400° C. and a withstand pressure is 300 MPa.

An aqueous solution containing 0.33 M of glycerin and 0.25 M of sodium hydroxide was prepared. The obtained aqueous solution was poured into the reactor (10), followed by air-tightly sealing. A packing ratio of the solution was made not more than 60% by volume of the reactor (10).

Then, the reactor (10) was immersed in a heating shaker shown in FIG. 6 and shaken for a predetermined time.

A schematic diagram of the heating shaker is shown in FIG. 6. The heating shaker has a molten salt bath (21), a heater (22), an agitator (23), a temperature controller (24) and a thermocouple (25). The heating shaker can be controlled to a temperature in the range of 170 to 400° C. using the temperature controller (24) and the thermocouple (25).

A reaction temperature and a reaction time in the heating shaker were 300° C. and 60 min, respectively. The pressure was made saturated vapor pressure of water at 300° C.

After performing the heating process, the reaction solution was immersed in cold water to rapidly cool.

After performing the cooling, a solution filled in the reactor (10) was taken out, followed by removing a solid component with a 0.45 μm filter, further followed by controlling the pH to neutrality with sulfuric acid and the neutralized solution was analyzed with high-performance liquid chromatography.

Here, the decomposition ratio of glycerin and the conversion ratio to a product thereof are defined as follows based on an amount of carbon in the substance.

Conversion ratio(% C)=carbon amount in a product/carbon amount in the starting glycerin×100

Decomposition ratio(% C)=carbon amount in decomposed glycerin/carbon amount in the starting glycerin×100

Analysis results by the high-performance liquid chromatography are shown in FIG. 7 (detector: absorption detector (UV)) and the decomposition ratios and the conversion ratios obtained based on detected substances in a reaction solution are shown in Table 1 below.

TABLE 1

| Detected Substance | Decomposition Ratio (% C) | Conversion Ratio (% C) |
|---|---|---|
| Glycerin (unreacted) | 59.8 | — |
| Lactic acid | — | 58.6 |
| Formic acid | — | 0.5 |
| Acetic acid | — | 0.3 |
| Acrylic acid | — | 0.1 |

From results of the high-performance liquid chromatography shown in FIG. 7, the following substance can be detected in a reaction solution: unreacted glycerin, lactic acid that is a main product and formic acid, acetic acid and acrylic acid, which are by-products. The decomposition ratio of glycerin was 59.8% C and the conversion ratio to lactic acid was 58.6% C. From the results, it is obvious that glycerin could be efficiently converted to lactic acid.

Example 2

In example 2, the reaction time was variously altered and the decomposition ratios of glycerin and the conversion ratios thereof to lactic acid were measured. Other conditions were the same as those of example 1.

Results of example 2 are shown in Table 2 below. FIG. 8 is obtained by charting results of Table 2.

From Table 2 and FIG. 8, it is found that, as the decomposition of glycerin proceeds, an amount of generated lactic acid increases.

TABLE 2

| Reaction Time (min) | Decomposition Ratio (% C) | Conversion Ratio (% C) |
|---|---|---|
| 5 | 16.0 | 6.6 |
| 10 | 19.5 | 14.5 |
| 30 | 43.0 | 39.4 |
| 60 | 59.8 | 58.6 |

Example 3

In example 3, in order to investigate the stability of lactic acid in alkaline water at a high temperature and a high pressure, an experiment of hydrothermal decomposition of lactic acid with alkaline component was carried out. Reaction conditions such as a temperature, a pressure and so on were made the same as those in example 1. FIG. 9 shows results thereof. As obvious from FIG. 9, it was found that lactic acid was very stable under an alkaline hydrothermal condition.

Example 4

In example 4, a hydrothermal decomposition of glycerin was carried out in a neutral aqueous solution without adding an alkaline component. A reaction temperature was made 300° C. and a reaction time was made 10 min. FIG. 10 shows the results thereof. FIG. 11 shows a result of the high-performance liquid chromatography after the reaction.

From FIG. 10, lactic acid was not generated in the hydrothermal reaction under neutral conditions. Furthermore, from FIG. 11, it was found that acrylic acid, acrolein and so on were generated. Thus, it was found that the reaction had to be carried out under the alkaline condition in order to obtain lactic acid.

Example 5

In example 5, a tube (10a) made of SUS316 as shown in FIG. 12 and capable of air-tightly sealed with caps (10b) made of the same SUS316 at both ends thereof was used as a reactor (10). The tube (10a) of the reactor (10) has a dimension of outer diameter: 12.7 mm, thickness: 1 mm and length: 111.3 mm, a volume of 10 ml, the allowable temperature limit of 400° C., and the withstand pressure of 30 MPa. To one end of the tube (10a), a line (10c) is connected. The line (10c) is connected to a high-pressure valve (10d). The reactor (10) is closed when the high-pressure valve (10d) is closed. when the high-pressure valve (10d) is opened, a gas component generated in the reactor (10) is externally taken out through the line (10c).

An experiment was carried out with the reactor (10) according to a procedure below.

(1) An aqueous solution was prepared by adding glycerin and NaOH to water so as to be a glycerin concentration: 0.33 M and an NaOH concentration: 0.25 M.

(2) The aqueous solution of the (1) was charged in the reaction tube (10) so that a volume is 40% by volume.

(3) In order to inhibit a solute from being oxidized during the reaction, the aqueous solution was deaerated and air in the reaction tube (10) was substituted by nitrogen gas.

(4) The reactor (10) was sealed intimately by closing the high-pressure valve (10d) and immersed in a molten salt bath (21) (FIG. 13) of a heating shaker (20) kept at a predetermined temperature to start a reaction. The reaction temperature was set at 300° C. In FIG. 13, the molten salt bath (21), the heater (22), the temperature controller (24) and the thermocouple (25) are the same as those of the heating shaker (20) shown in FIG. 6; accordingly, detailed explanations thereof are omitted here. A reference numeral (26) in FIG. 13 denotes a shaker. As a downward-extended crank-like rotation bar (26a) is rotated, a horizontal bar (26b) moves in a horizontal direction. The reactor (10) suspended at portions of caps (10b) to the horizontal bars (26b) is horizontally shaken.

(5) After heated and shaken over for 60 min, the reactor (10) is taken out from the heating shaker and rapidly cooled in cooling water.

(6) A generated gas was recovered and gas components thereof were analyzed by gas chromatography (GC).

(7) A reaction solution in a tube (10a) of the reactor (10), after controlling the pH to 7 to 8, was filtered with a 0.45 μm filter to remove a solid.

(8) Components of a filtrate were analyzed by high-performance liquid chromatography (HPLC).

In FIGS. 14 and 15, HPLC analysis results of reaction products are shown. A graph of FIG. 14 was obtained by measuring the absorbance of UV and a graph of FIG. 15 was obtained by measuring the refractive index.

As obvious from FIG. 14, the reaction product was almost made of lactic acid that is a target substance. Other reaction products included acetic acid and acrylic acid. These are considered to be generated by further decomposing lactic acid; accordingly, as the reaction time becomes longer, production ratios thereof are considered to be higher. Furthermore, as shown in the graph of FIG. 15, the glycerin partially remains unreacted.

As the result of component analysis of the generated gas (by GC), almost all was hydrogen ($H_2$) gas and carbon monoxide (CO), carbon dioxide ($CO_2$), oxygen ($O_2$) and the like were not detected.

Example 6

In the example, variations with time of the reaction products were measured. The reaction conditions were made the same as those of example 5 except that an NaOH concentration was set to 1.25 M and, a reaction solution was subjected to a HPLC analysis and a GC analysis at the start of the reaction and at 20, 40, 60, 80 and 100 min after the start of the reaction and the residual ratio of glycerin and yields of lactic acid and hydrogen at each of times are measured.

The yield of lactic acid(mol %) and the residual ratio of glycerin (mol %) were calculated according to formulas below.

Yield of lactic acid(mol %)=amount of reaction product (mol/L)/amount of supplied glycerin(mol/L)×100

Residual ratio(mol %)=amount of unreacted glycerin (mol/L)/amount of supplied glycerin(mol/L)×100

Obtained results are shown in FIG. 16.

As shown in FIG. 16, the yield of lactic acid reached substantially 90% at 90 min after the start of the reaction. The yield of hydrogen as well showed substantially the same behavior as that of lactic acid. Furthermore, at the respective times, the yields of lactic acid were substantially the same as the decomposition ratio of glycerin ((100-residual ratio) %). That is, it is found that glycerin was oxidized by dehydration by the alkaline hydrothermal reaction to convert almost portion into lactic acid and hydrogen. On the other hand, since acid (lactic acid) is generated from alcohol (glycerin) by the reaction, NaOH is consumed to neutralize. The above matters can be expressed by a stoichiometric formula (1) below.

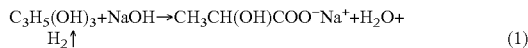

$$C_3H_5(OH)_3 + NaOH \rightarrow CH_3CH(OH)COO^-Na^+ + H_2O + H_2\uparrow \quad (1)$$

The stoichiometric formula shows that NaOH equal mole as that of glycerin is necessary in order to forward a reaction 100%.

Example 7

In the example, a variation with time of the yield of lactic acid was measured using several samples each of which has a variant NaOH concentration from 0 to 2.5 M.

As for the experimental conditions, a reaction temperature was made 300° C. and a glycerin concentration was made 0.33 M. The yield of lactic acid was measured at the start of the reaction and at 30, 60, 90, 120 and 150 min after the start of the reaction. The yield of lactic acid was obtained by calculating similarly to the example 6. Obtained results are shown in FIG. 17.

As shown in FIG. 17, when the NaOH concentration was 0 M, lactic acid was not detected and instead thereof acrolein that is a product generated by dehydration of glycerin was detected. Furthermore, with an increase in the alkaline concentration, a rate of generation of lactic acid increased and the yield of lactic acid after 90 min reached substantially 90% when the NaOH concentration was 1.25 M. Thus, it is thought that the alkaline component equal to or more than equivalent mole plays a very important role in the reaction.

Example 8

In the example, a variation with time of the yield of lactic acid was measured using several temperature conditions varied in the range of 220 to 340° C. As for the experimental conditions, the NaOH concentration was made 1.25 M and the glycerin concentration was made 0.33 M. The yield of lactic acid was measured at the start of the reaction and at 20, 40, 60, 80 and 100 min after the start of the reaction. The yield of lactic acid was obtained by calculating similarly to example 6. Obtained results are shown in FIG. 18.

As shown in FIG. 18, when the reaction temperature was 220° C. and the reaction time was 1 hr, the generation of lactic acid was confirmed only slightly. Furthermore, it was found that lactic acid could be produced by continuing the reaction for a long time even when the temperature was 150° C. Still furthermore, with an increase of the reaction temperature, the rate of generation of lactic acid increased and the yield of lactic acid reached substantially 90% at 300° C. and 90 min. When the reaction temperature was 340° C., the yield reached 80% at 10 min; however, the yield decreased thereafter. It is considered that lactic acid is remarkably decomposed at a temperature more than 300° C. Acetic acid and acrylic acid were detected as products generated by decomposition of lactic acid under the condition for the alkaline hydrothermal reaction.

EXPLANATION OF REFERENCE NUMERALS

Figure 1:
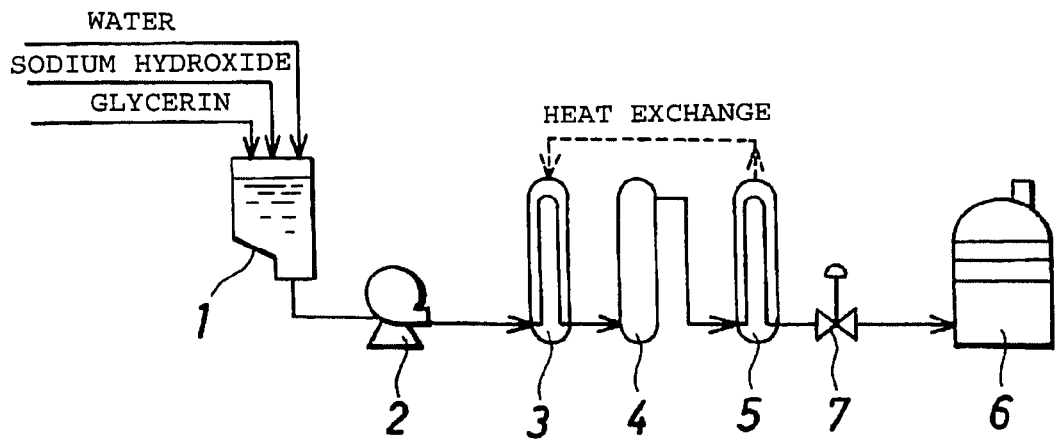
FIG. 1 is a flow sheet for explaining a process for producing lactic acid according to embodiment 1.
Figure 2:
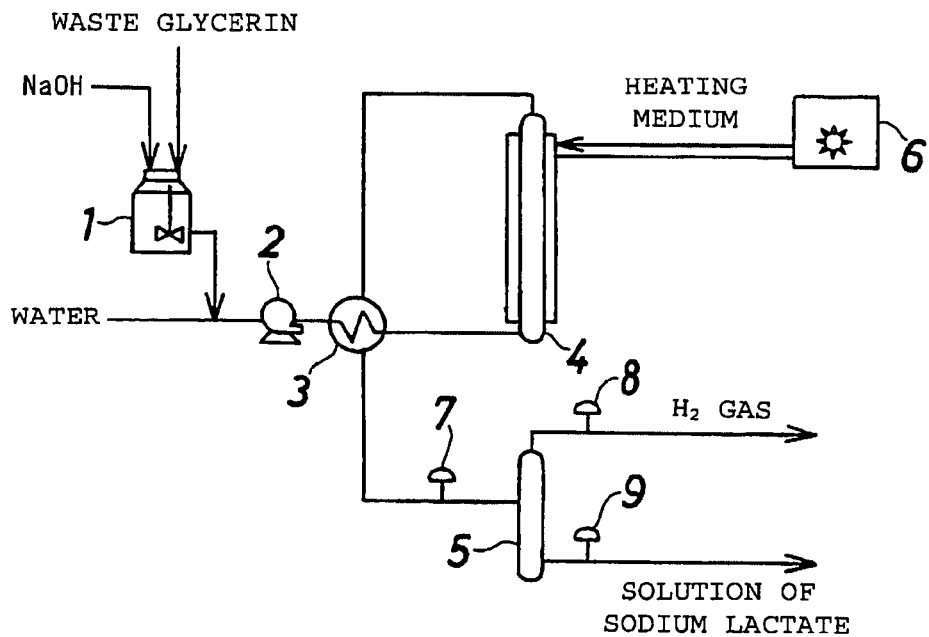
FIG. 2 is a flow sheet for explaining an apparatus for producing lactic acid according to embodiment 2.
Figure 3:
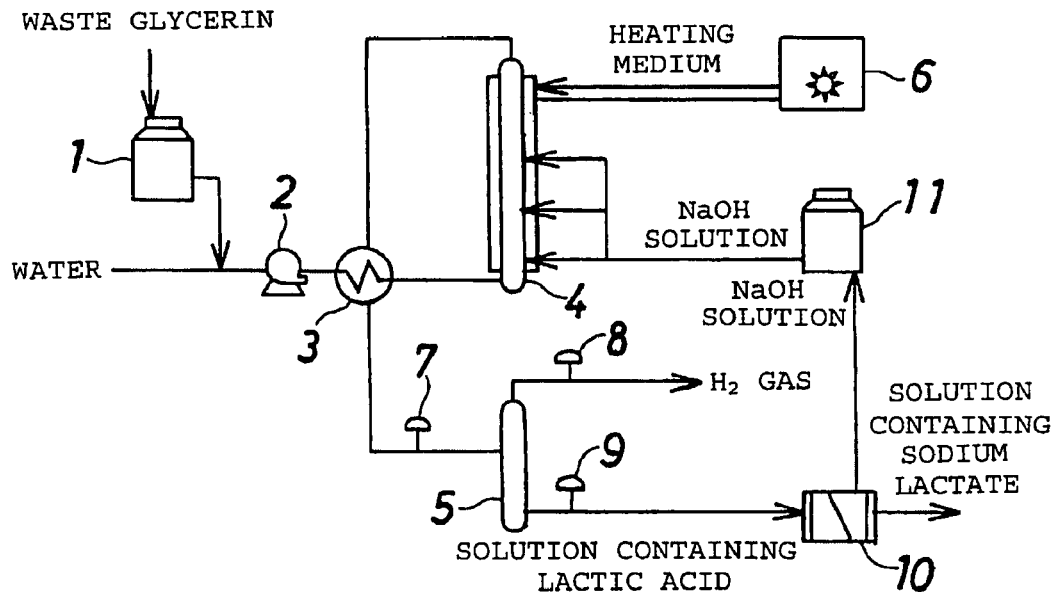
FIG. 3 is a flow sheet for explaining an apparatus for producing lactic acid according to embodiment 3.
Figure 4:
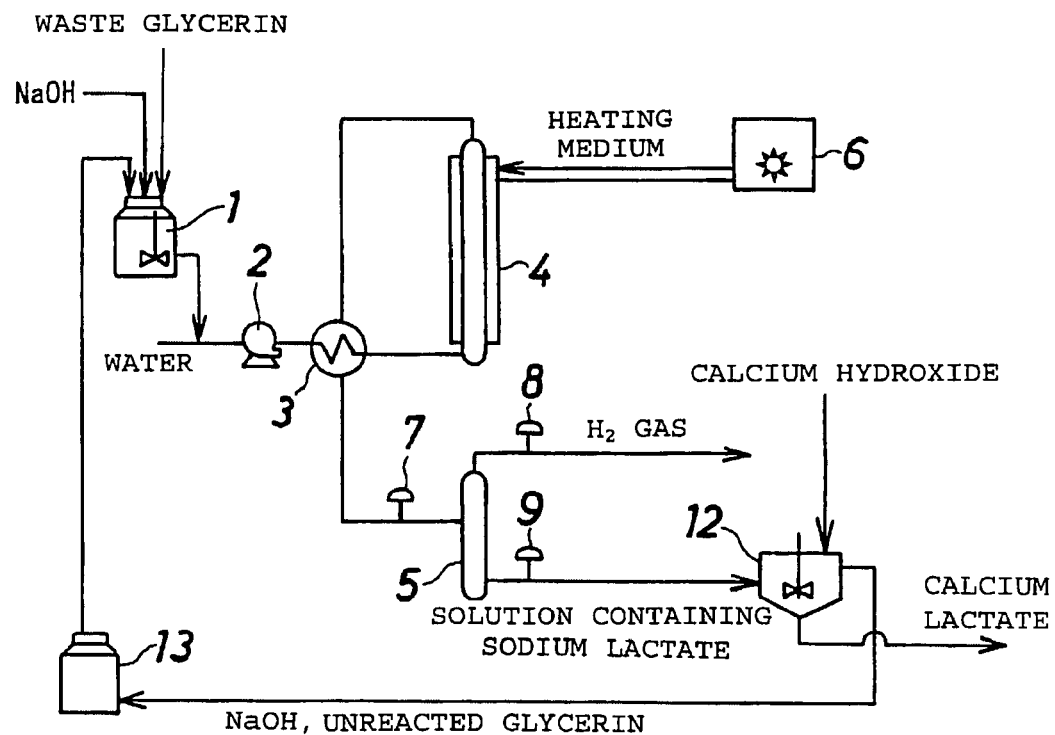
FIG. 4 is a flow sheet for explaining an apparatus for producing lactic acid according to embodiment 4.
Figure 5:
FIG. 5 is a schematic diagram showing a reactor used in example 1.
Figure 6:
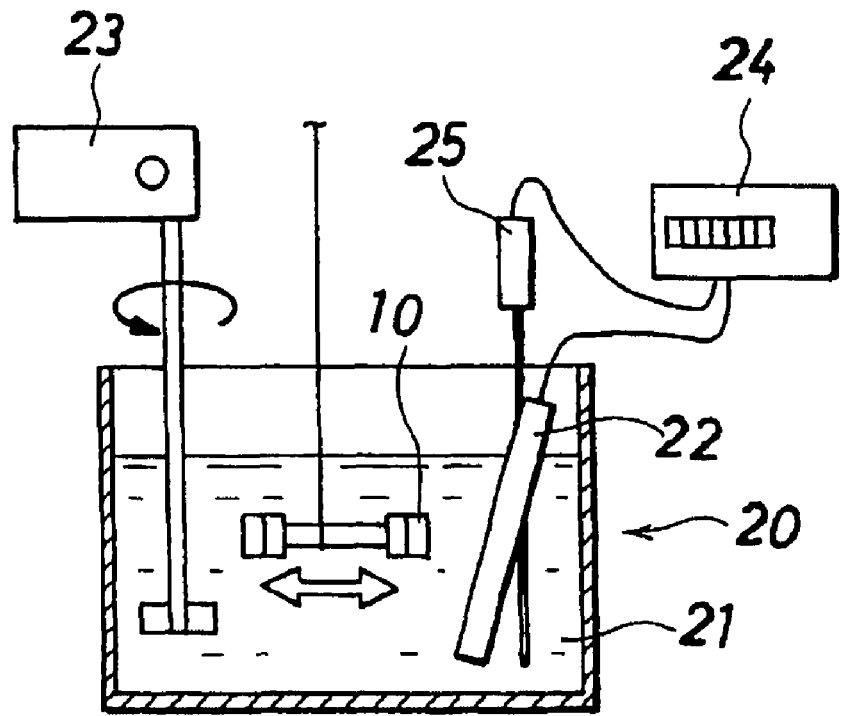
FIG. 6 is a schematic diagram showing a heating shaker used in example 1.
Figure 7:
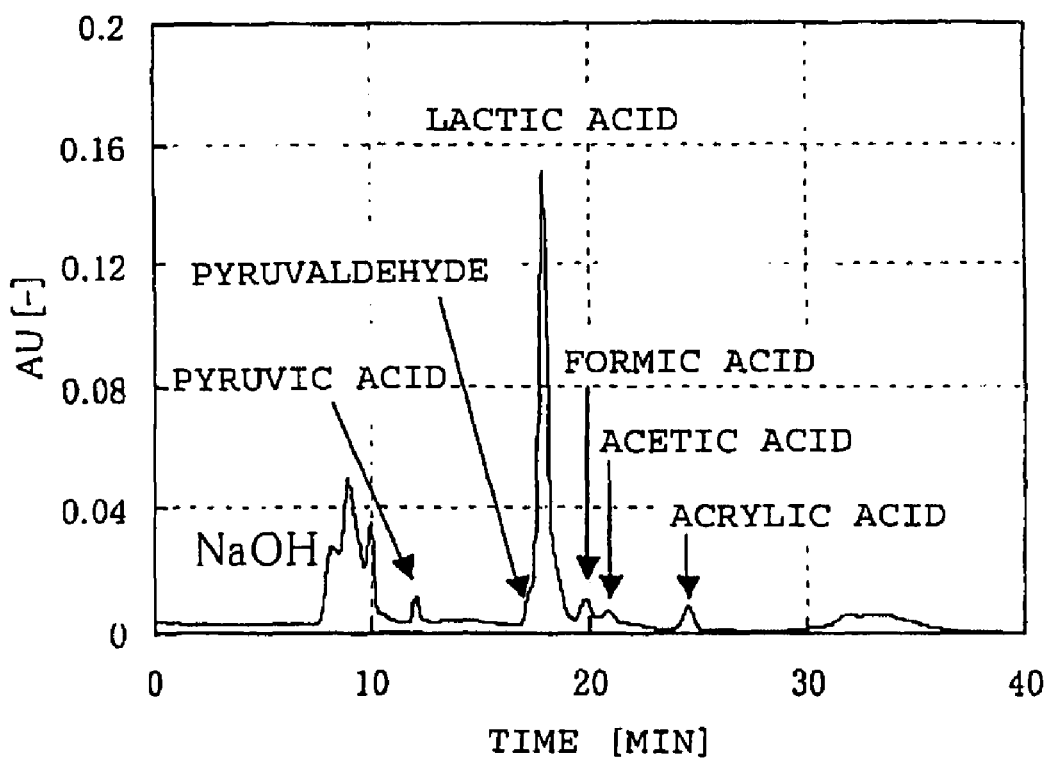
FIG. 7 is a graph of high-performance liquid chromatography analysis showing results of example 1 with an absorbance detector (UV) as a detector.
Figure 8:
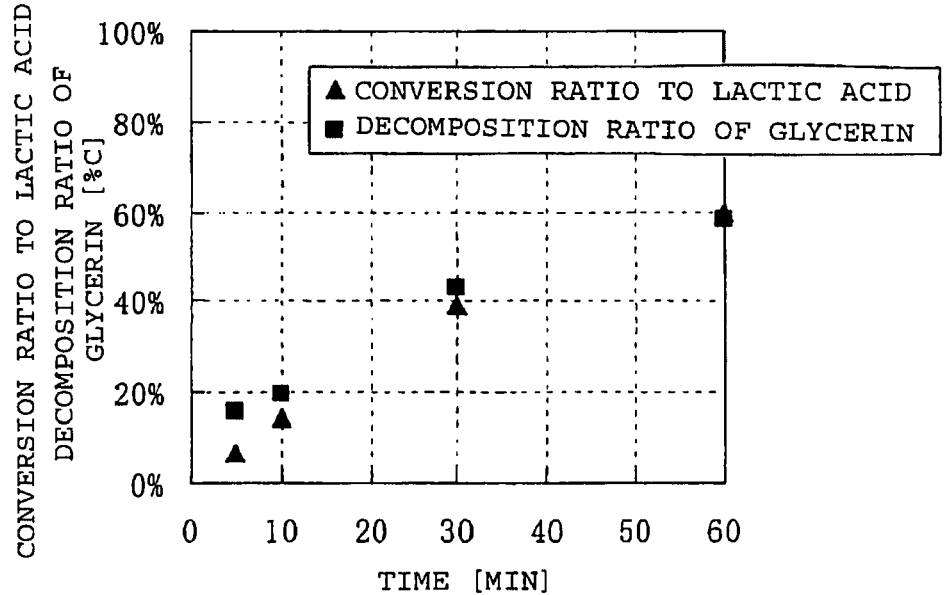
FIG. 8 is a graph showing results of example 2.
Figure 9:
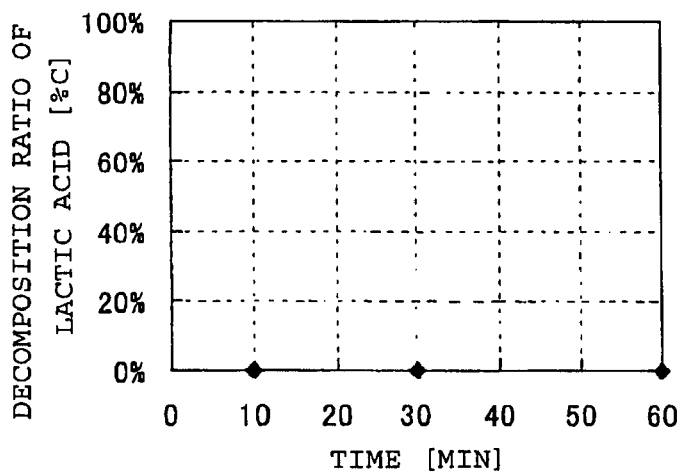
FIG. 9 is a graph showing results of example 3.
Figure 10:
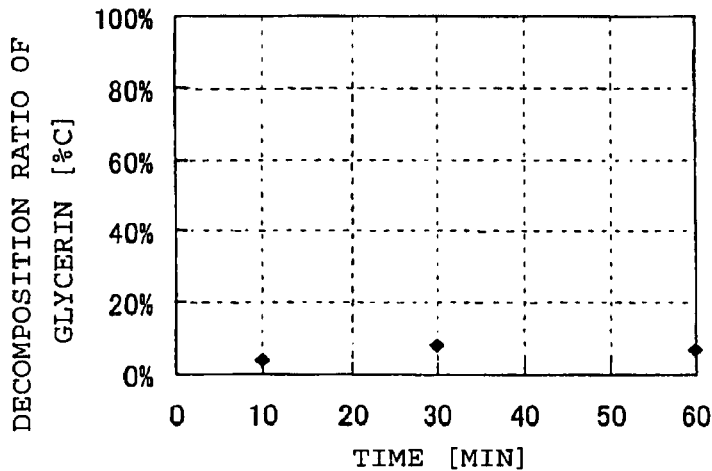
FIG. 10 is a graph showing results of example 4.
Figure 11:
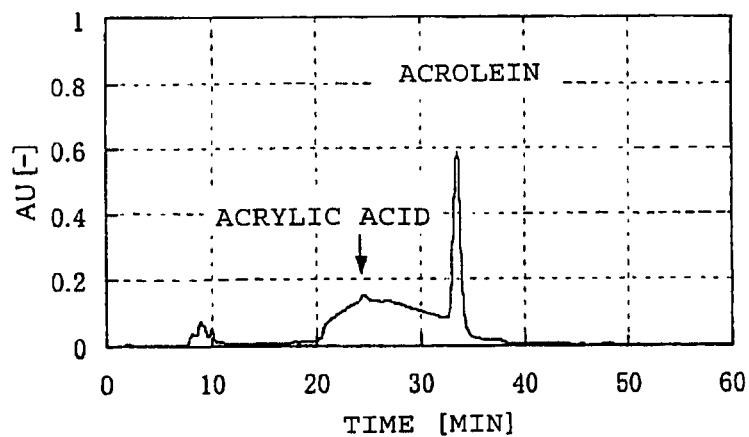
FIG. 11 is a graph showing high-performance liquid chromatography analysis after a reaction of example 4.
Figure 12:
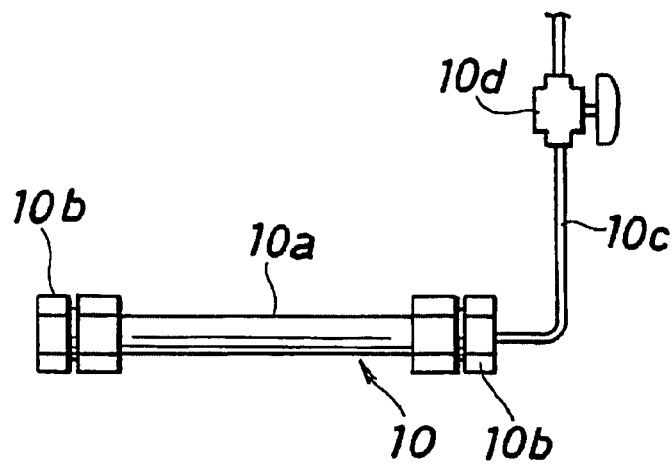
FIG. 12 is a schematic diagram showing a reactor that is used in example 5.
Figure 13:
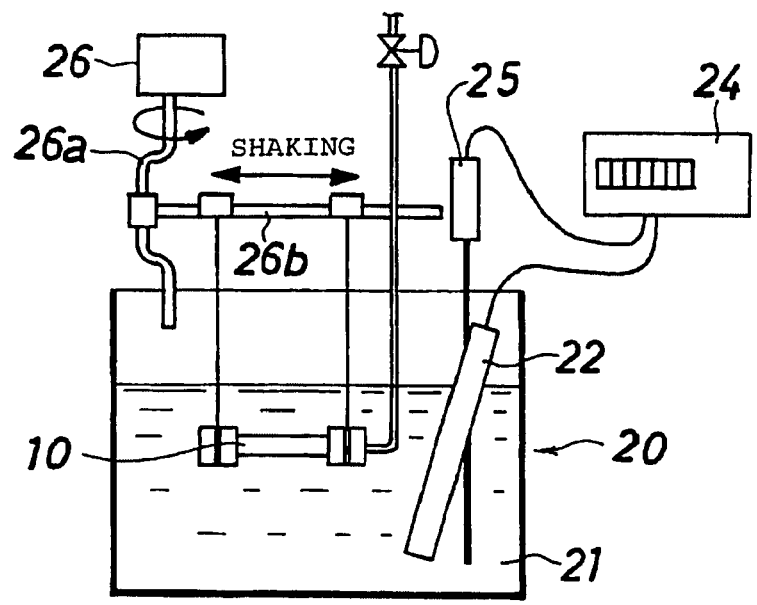
FIG. 13 is a schematic diagram showing a heating shaker that is used in example 5.
Figure 14:
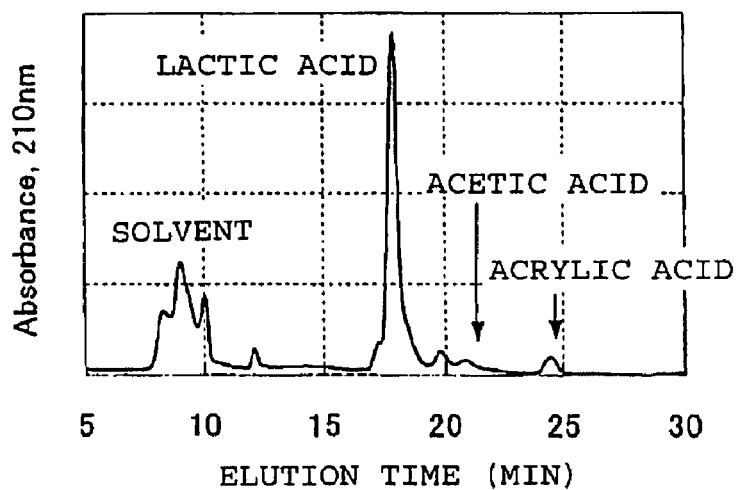
FIG. 14 is a graph of high-performance liquid chromatography analysis showing results of example 5.
Figure 15:
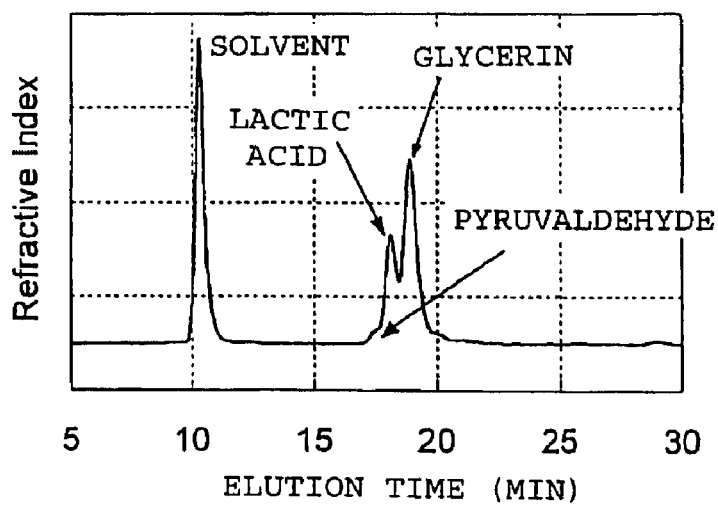
FIG. 15 is a graph of high-performance liquid chromatography analysis showing results of example 5.
Figure 16:
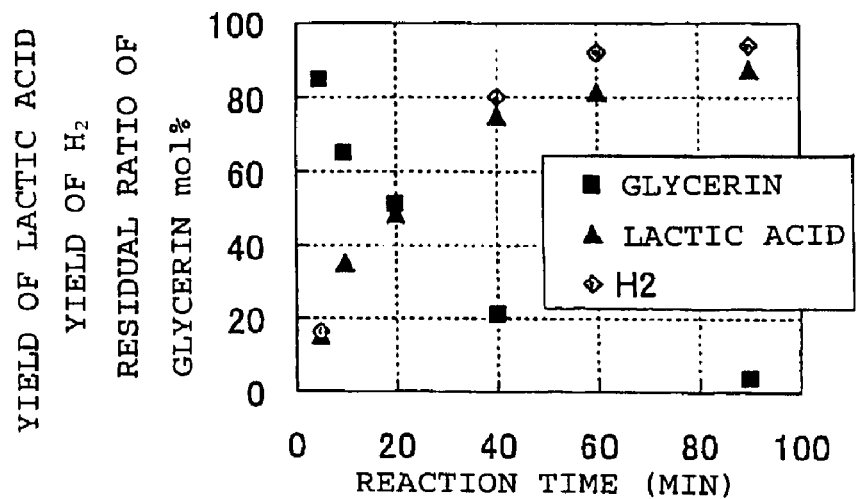
FIG. 16 is a graph showing results of example 6.
Figure 17:
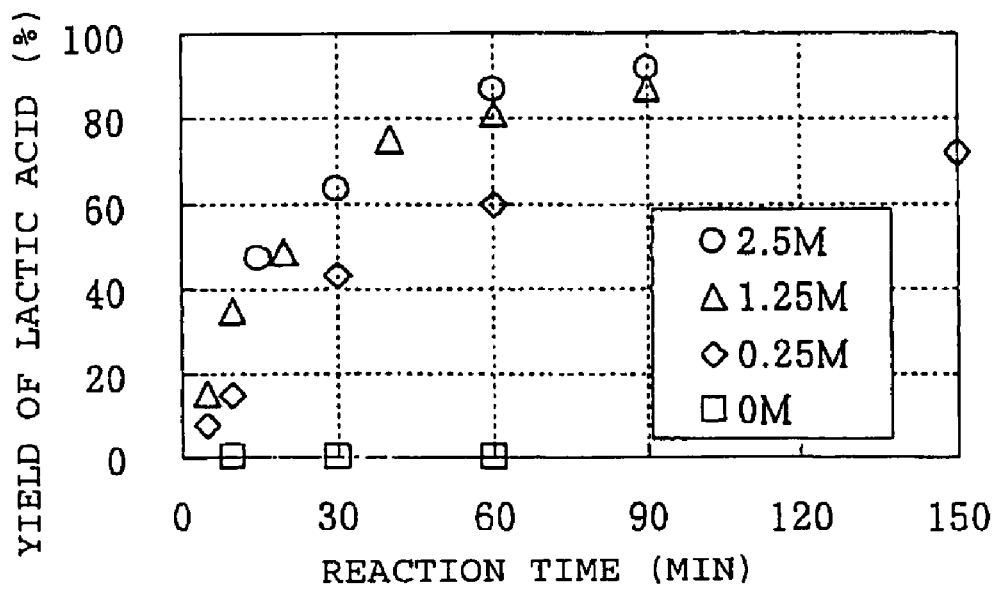
FIG. 17 is a graph showing results of example 7.
Figure 18:
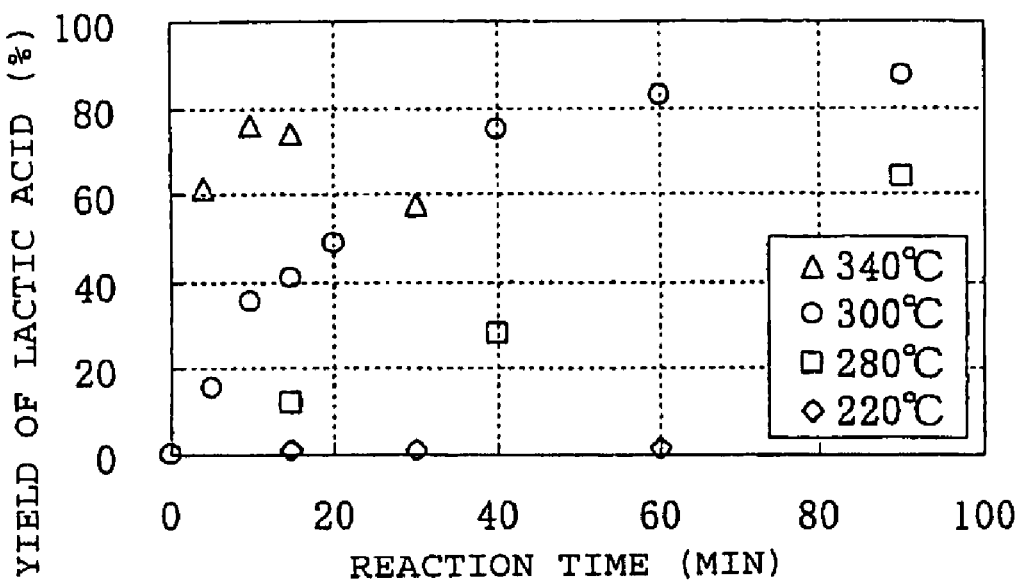
FIG. 18 is a graph showing results of example 8.

1: tank for storing a raw material
2: high-pressure pump
3: pre-heater
4: reaction column
5: cooler
6: tank for storing an alkaline solution containing lactic acid

The invention claimed is:

1. A process for producing lactic acid, comprising subjecting glycerin in an alkaline solution consisting of glycerin, an alkaline component and water to a hydrothermal reaction under an alkaline condition.

2. The process according to claim 1, wherein the hydrothermal reaction is carried out wherein a reaction temperature is in a range of from 280 to 340° C., a pressure is in a range of from 1 to 30 MPa, and equal to or more than a saturated vapor pressure at the reaction temperature such that the water is in a liquid phase state, and an alkaline concentration within the solution is 1 to 5 times a glycerin concentration.

3. The process for producing lactic acid according to claim 1, wherein the glycerin as a starting material is obtained from plant fats, animal fats or a pure product synthesized chemically.

4. The process for producing lactic acid according to claim 1, wherein a raw material is obtained from a discharge comprising the glycerin generated in production of a diesel fuel oil from fats, in which the fats are subjected to a transesterification reaction with an alcohol in the presence of an alkaline catalyst in order to obtain a fatty acid ester.

5. The process according to claim 1, further comprising separating an alkaline solution comprising the lactic acid from a hydrogen gas, wherein the hydrogen gas is generated in the hydrothermal reaction.

6. The process for producing lactic acid according to claim 1, further comprising concentrating the lactic acid and an alkaline component present in an aqueous solution after the hydrothermal reaction according to an electrodialysis process.

7. The process for producing lactic acid according to claim 1, further comprising separating the lactic acid from an alkaline component present in an aqueous solution after the hydrothermal reaction according to an electrodialysis process with a bipolar membrane.

8. The process for producing lactic acid according to claim 1, further comprising separating a solid of lactate salt from an alkaline component present in an aqueous solution after the hydrothermal reaction according to a crystallization process.

9. The process for producing lactic acid according to claim 1, wherein an alkaline component for making the glycerin under an alkaline condition is supplied when a hydrothermal reaction is carried out.

10. The process according to claim 9, comprising supplying the alkaline component a few times.

11. The process according to claim 9, comprising separating the alkaline component from the alkaline solution comprising lactic acid.

12. The process according to claim 7, comprising recovering unreacted glycerin dissolved in the solution comprising the alkaline component in order to reuse the recovered glycerin as a raw material.

13. The process according to claim 5, wherein the generated hydrogen gas is used for a fuel battery.

14. The process according to claim 1, wherein the hydrothermal reaction is carried out wherein a reaction temperature is higher than 280 and equal or less than 340° C.

* * * * *